(12) United States Patent
Lutze

(10) Patent No.: US 7,927,495 B2
(45) Date of Patent: Apr. 19, 2011

(54) SEPARATION AND CLEANING OF A SUSPENSION COMPRISING MAGNETIC MICROPARTICLES

(75) Inventor: Konstantin Lutze, Mannedorf (CH)

(73) Assignee: Qiagen Instruments AG, Hombrechtikon (CH)

( * ) Notice: Subject to any disclaimer, the term of this patent is extended or adjusted under 35 U.S.C. 154(b) by 1290 days.

(21) Appl. No.: 10/597,036

(22) PCT Filed: Jan. 4, 2005

(86) PCT No.: PCT/CH2005/000001
§ 371 (c)(1), (2), (4) Date: Jul. 7, 2006

(87) PCT Pub. No.: WO2005/065831
PCT Pub. Date: Jul. 21, 2005

(65) Prior Publication Data
US 2007/0148785 A1    Jun. 28, 2007

(30) Foreign Application Priority Data
Jan. 8, 2004    (CH) ..................................... 0024/04

(51) Int. Cl.
*B01D 35/06* (2006.01)
*B03C 1/00* (2006.01)
*G01N 33/553* (2006.01)

(52) U.S. Cl. ........ 210/695; 210/222; 210/223; 436/526; 436/177; 436/806; 435/287.1; 435/287.2; 435/287.3; 422/65; 422/68.1; 422/501; 422/527

(58) Field of Classification Search .................. 436/526, 436/177, 806, 287.1, 287.2, 287.3; 422/65, 422/68.1, 100, 101, 501, 527; 210/222, 223, 210/695; 435/287.1, 287.2, 287.3
See application file for complete search history.

(56) References Cited

U.S. PATENT DOCUMENTS
5,055,263 A * 10/1991 Meltzer .......................... 422/65

FOREIGN PATENT DOCUMENTS
WO       WO 03090897 A1 * 11/2003
* cited by examiner

Primary Examiner — David A Reifsnyder
(74) Attorney, Agent, or Firm — Thaddius J. Carvis

(57) ABSTRACT

A device (10) is described for automatically separating solid and liquid phases of a suspension (78) and for purifying magnetic microparticles (76) loaded with organic, e.g., biological or biochemical substances. The device includes a process area (12) with devices, which move in a cyclic manner for transporting the magnetic microparticles (76) in the x-direction. A first guide (14) is used for supplying sample containers (P) in the x-direction and second guides (18) are used for supplying reagent containers (R) in the y-direction to the process area (12). The second guides (18) in the y-direction extend at an angle ($\alpha$) of 30 to 150° to the x-direction. A carrier element (24), including carrier plates (24a, 24b, 24c) can be moved back and forth in the x-direction and can be lifted and lowered in the z-direction. The reagent containers (R) can be positioned according to the grid of the transfer elements (28), shown configured as rod-shaped permanent magnets or electromagnets, by introduction into the process area (12), taking place at an angle ($\alpha$) and can be rejected by ejection in the same direction into a waste collector.

16 Claims, 9 Drawing Sheets

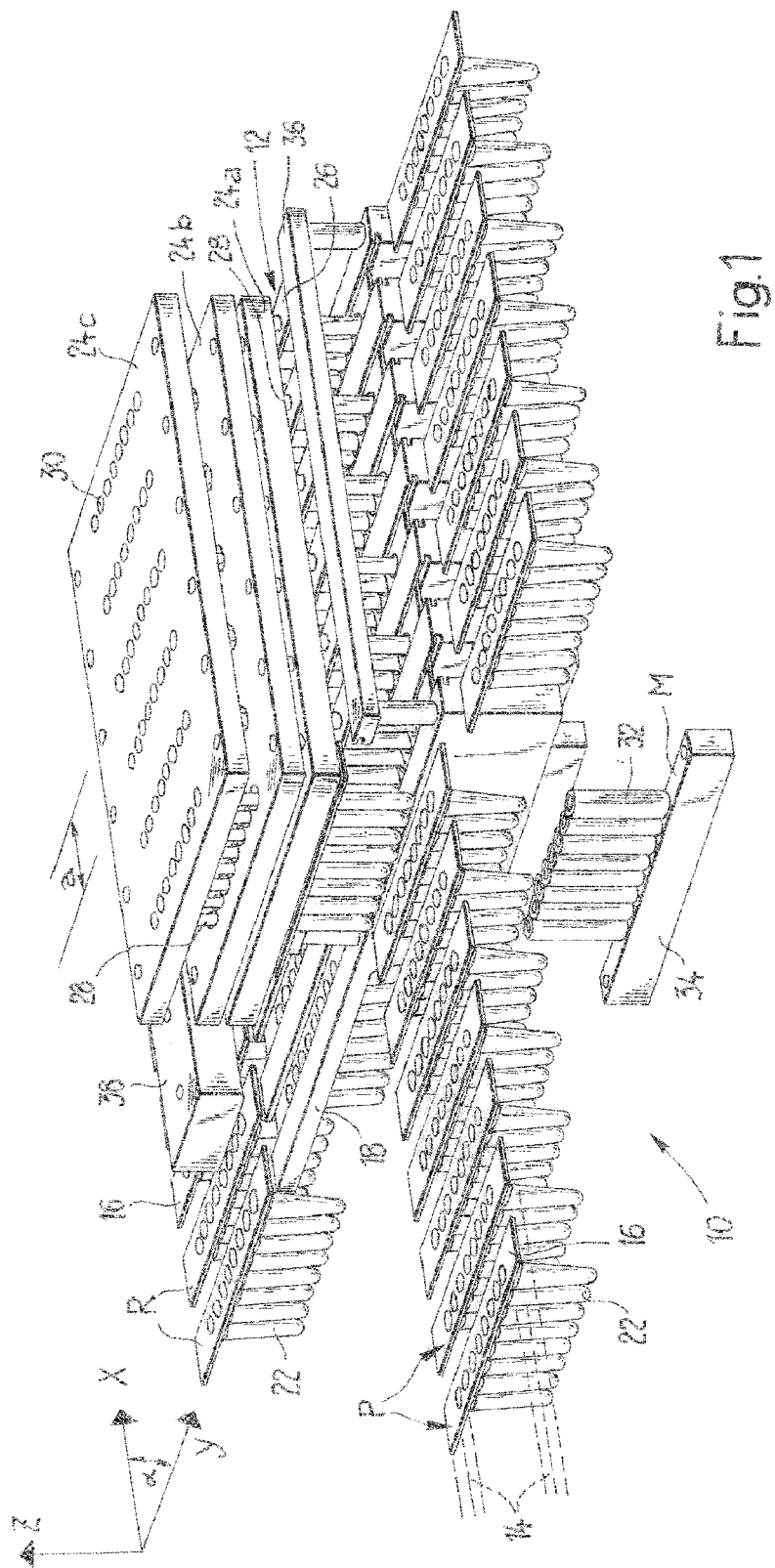

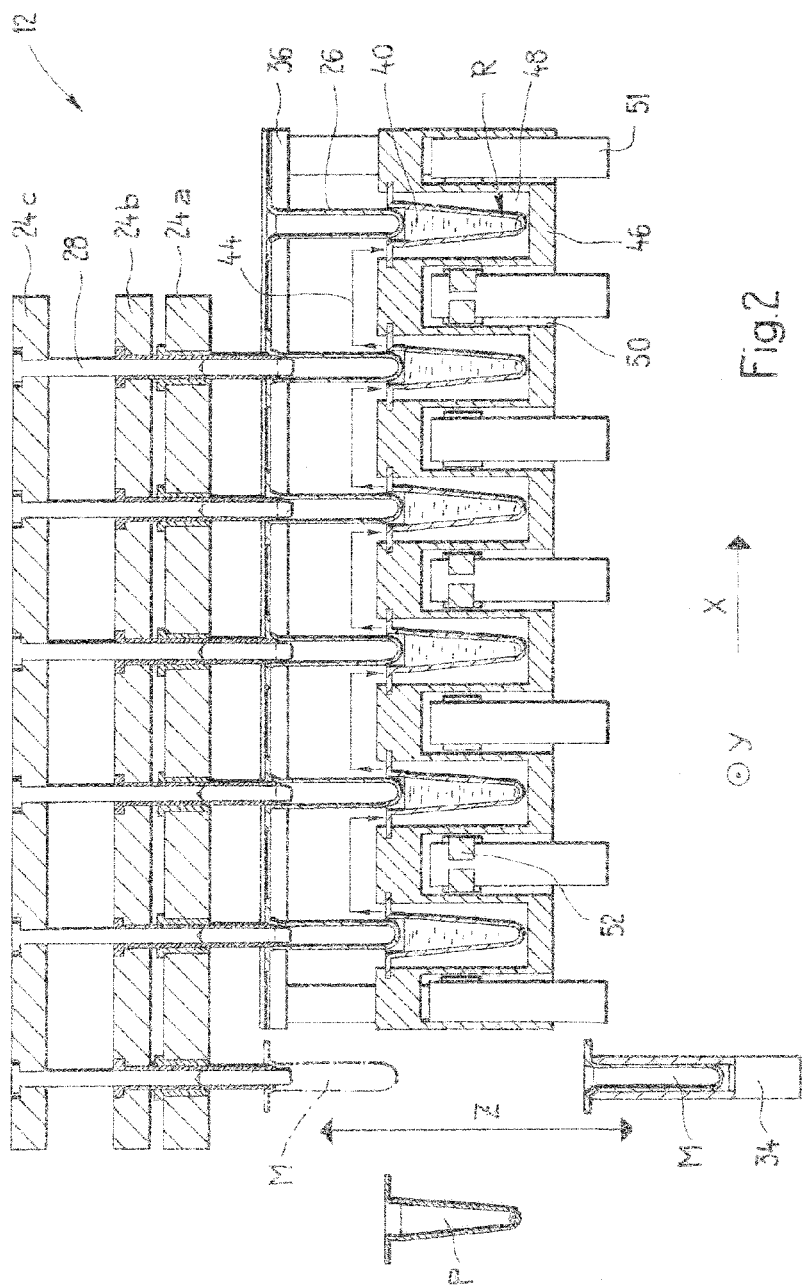

Figure 16:
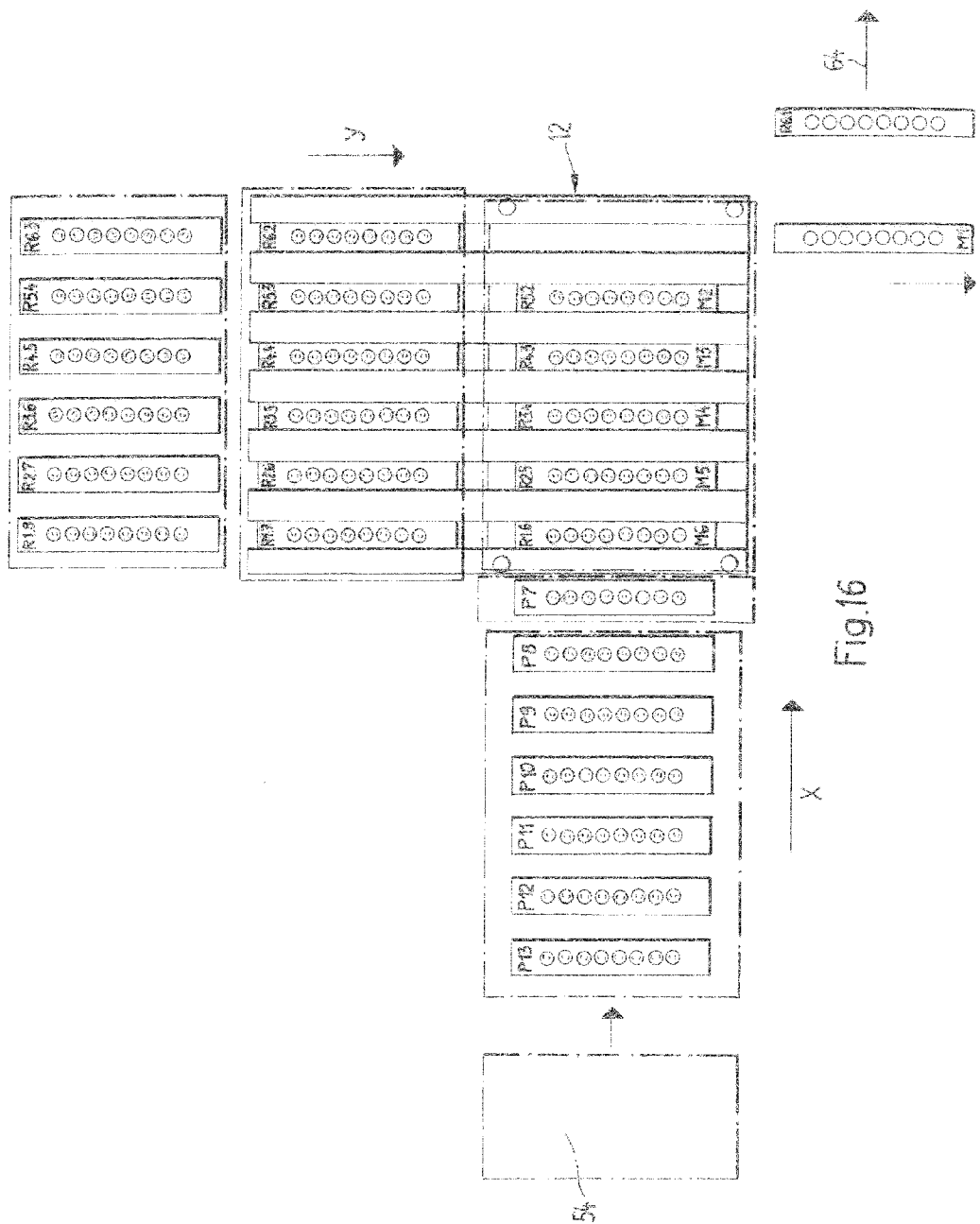

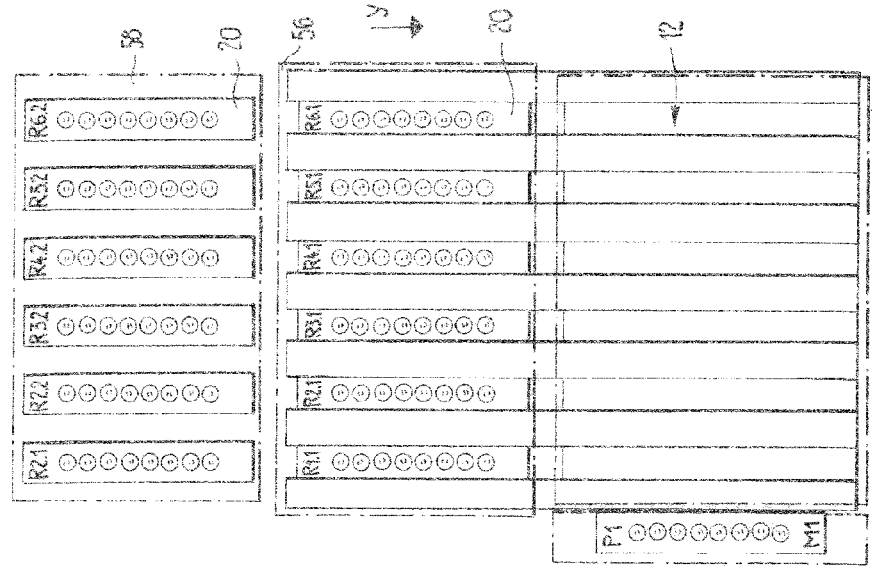
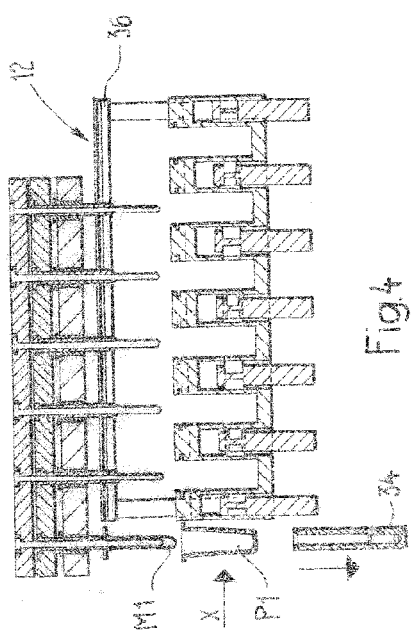

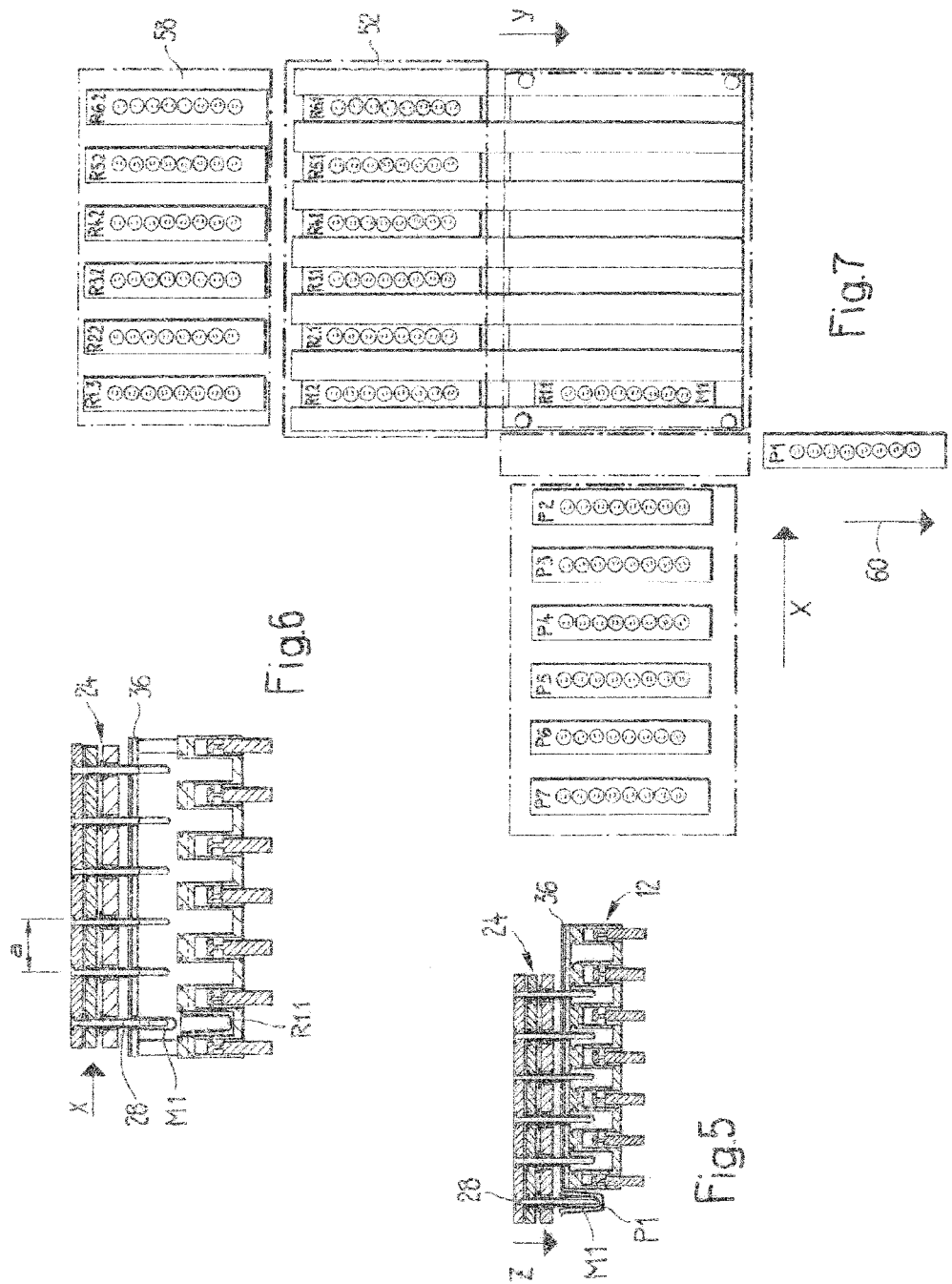

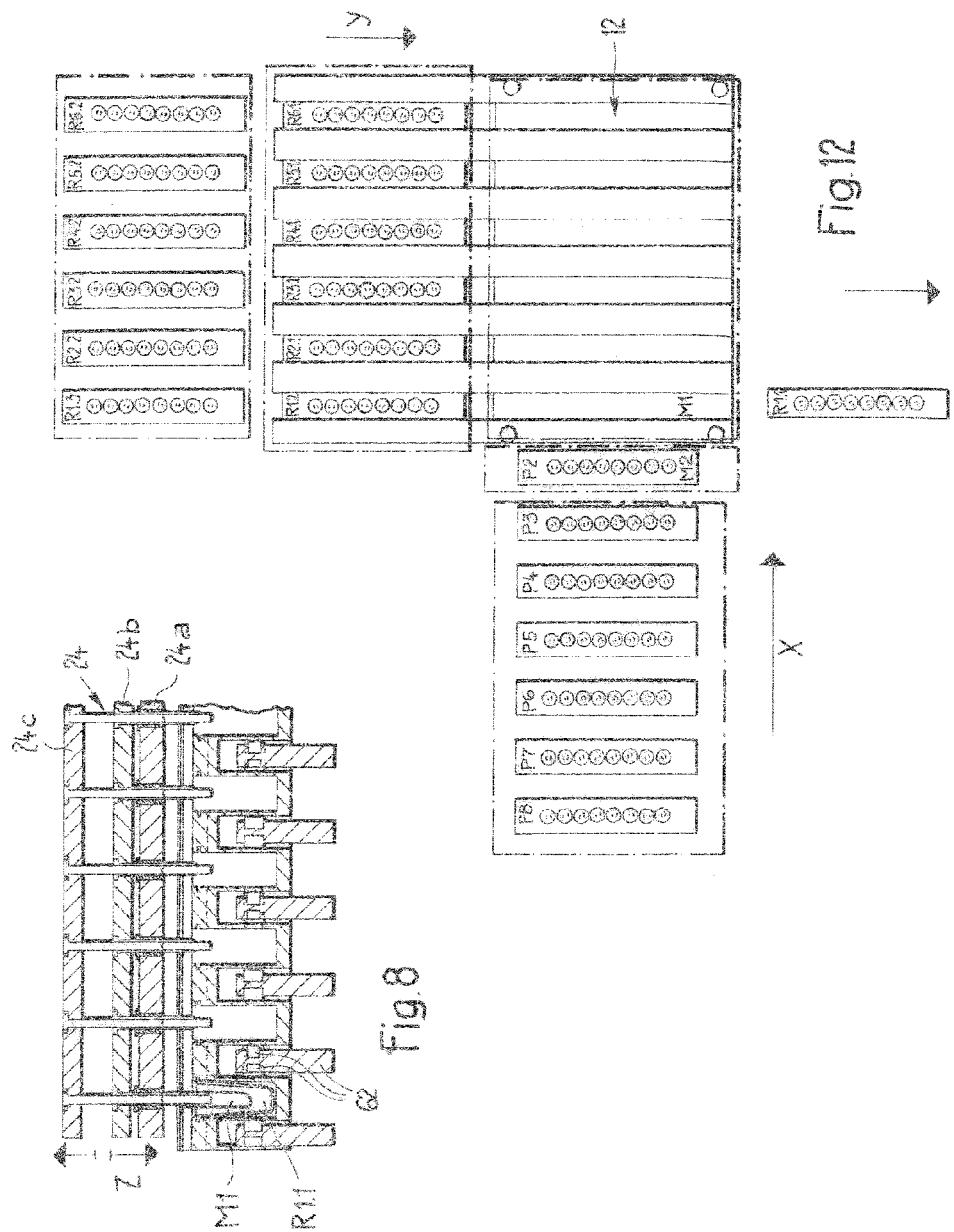

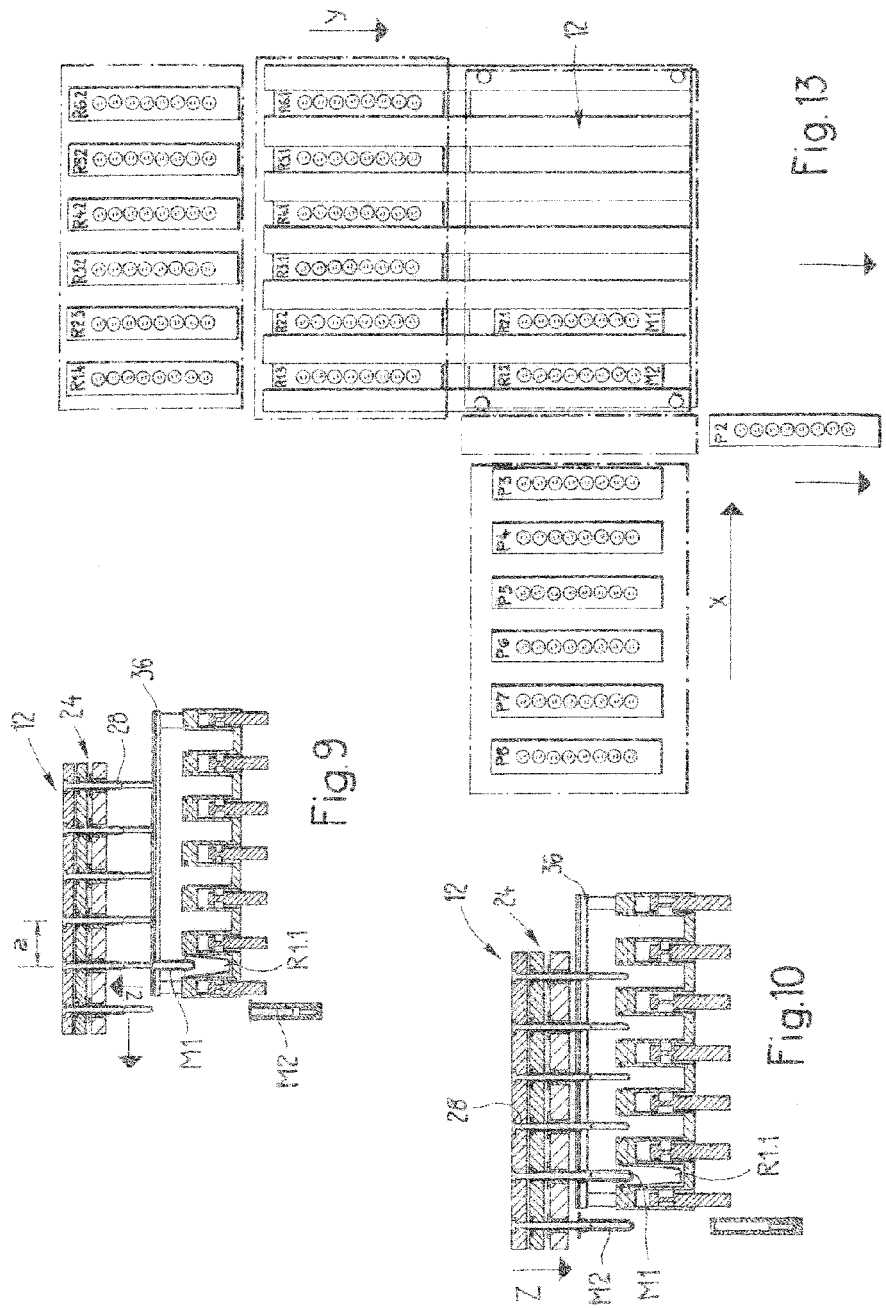

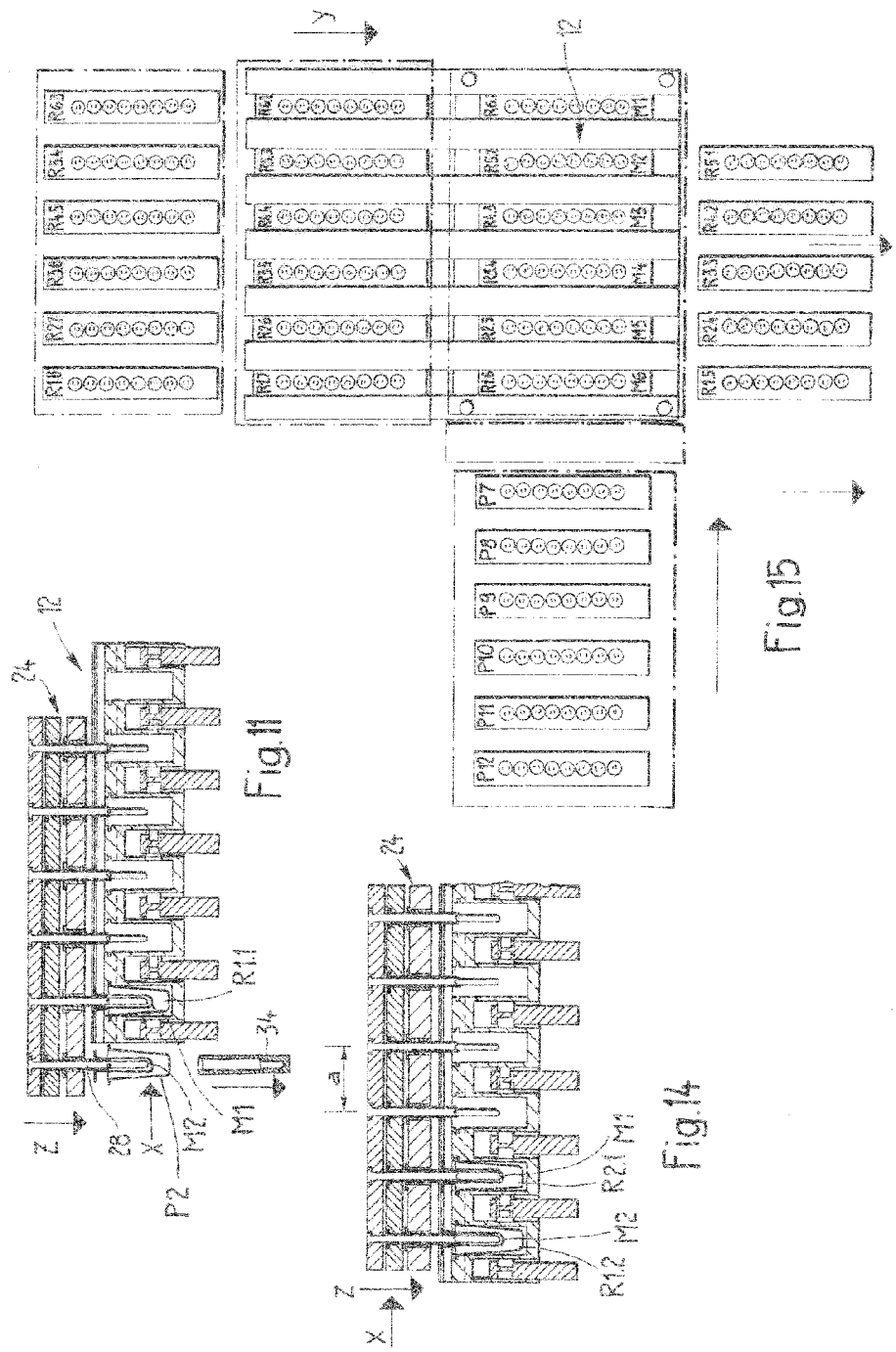

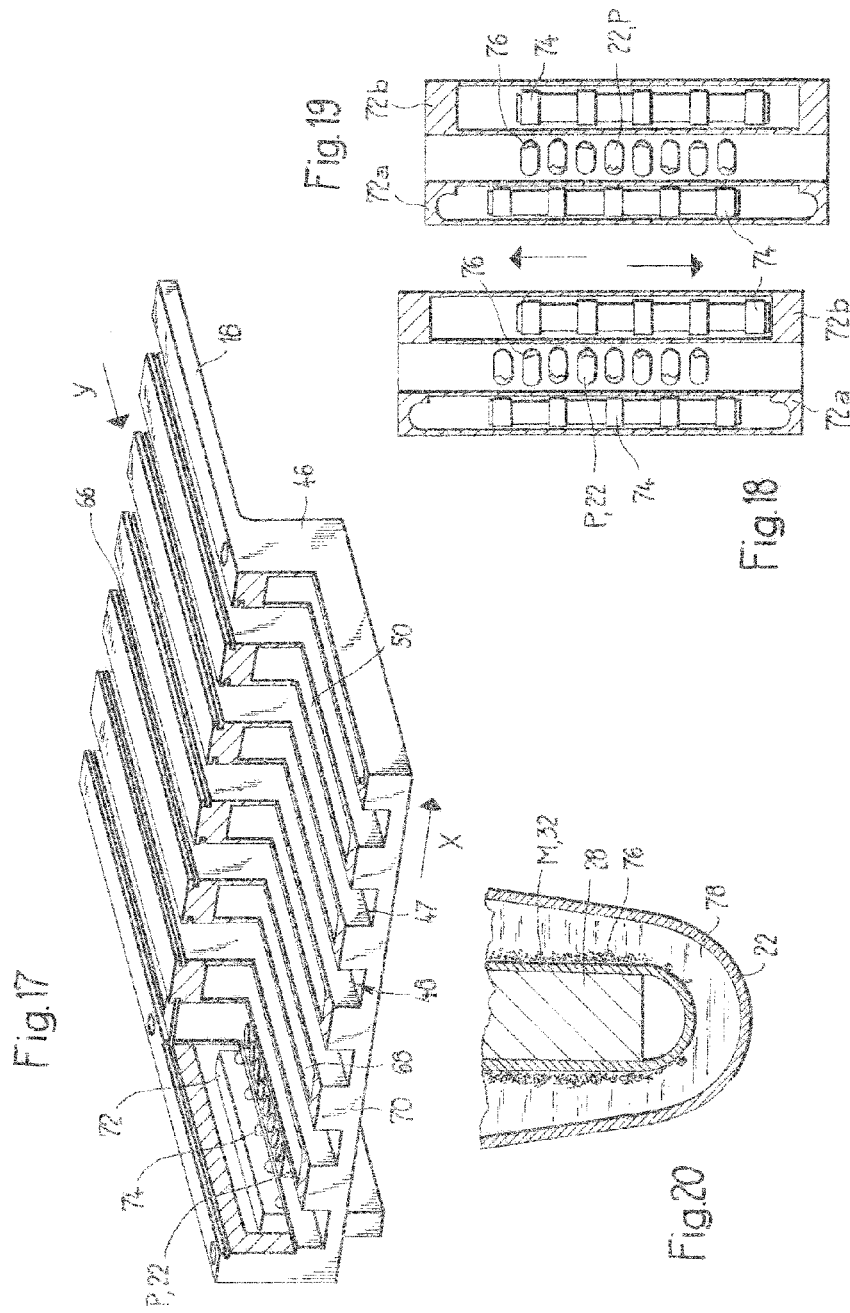

SEPARATION AND CLEANING OF A SUSPENSION COMPRISING MAGNETIC MICROPARTICLES

The invention relates to a device for the automatic separation of the solid and liquid phase of a suspension and for purifying magnetic microparticles loaded with organic, in particular molecular biological or biochemical substances, which device comprises a process area with mechanisms which move in a cyclic manner for transporting the magnetic microparticles in the x-direction. The invention also relates to sample and reagent containers for use in the device and a method for automatic separation and purification in the device.

The investigation and/or analysis of organic, in particular molecular biological substances by determining their chemical or physical properties with specifically developed methods is continuously increasing in importance. The use of an inert carrier in the form of microparticles is advantageous for the chemical analysis of molecular biological substances, for example blood or urine. If these microparticles consist of a magnetic or magnetisable material, contain a material such as this or are covered with such a material, the solid phase can be separated off from a suspension with a magnetic field and isolated by subsequent purifying or washing processes with a very high degree of cleanliness. Non-magnetic microparticles are sedimented, aspirated off or decanted, which makes comparatively complicated, long-lasting and/or frequent washing processes with at least one buffer solution necessary.

Loaded magnetic microparticles are separated off according to known methods, in particular, in that they are deposited by permanent magnets on the wall of a reaction vessel with the formation of a cluster and are fixed there during pipetting or decanting of the suspension liquid. During the removal of the suspension liquid, the magnetic field has to be maintained, which generally results in complicated methods and devices.

A method and a device for separating and washing magnetic solid particles which are arranged finely distributed in liquid samples is described in DE 3926462 A1.

The solid particles are loaded with organic substances as the precursor for a photometric or radiometric evaluation of patient samples in the case of immunoluminometric and immunoradiometric tests. The liquid samples are exposed in test tubes to a magnetic field generated by permanent magnets with the magnetic solid particles being attached to the inner wall of the test tubes. After a predetermined time, the residual liquid is aspirated off while maintaining the magnetic field. The separation and washing process is carried out fully automatically in a continuous process and a plurality of permanent magnets are arranged on a conveying section for the test tubes.

The separation method for depositing magnetic microparticles is improved according to EP 0806665 B1, in that according to one variant, the microparticles which are deposited on the vessel wall under the effect of a permanent magnet can be resuspended, after the rinsing water has been aspirated off, with fresh water or a fresh reagent, and this substantially increases the purification effect. After a certain dwell time, the microparticles are again attached under the magnetic effect of the wall of the reaction vessel and the rinsing water is aspirated off again. This process can be repeated many times.

U.S. Pat. No. 6,207,463 B1 disclosed a separation of magnetic microparticles from a suspension, in that a rod-shaped permanent magnet, which is covered by a protective layer except for the point, is dipped into the suspension with magnetic microparticles. The magnetic microparticles attach to the point of the transfer element and can be removed from the suspension solution when the rod is lifted, the cluster adheres to the rod and can be dipped into a new liquid phase. Thus pipetting or decanting can be omitted.

The inventor has set himself the object of providing a device and a method which allow a fully automatic process sequence and can be applied easily, rapidly, reliably and economically.

With reference to the device, the object is achieved according to the invention in that a first guide is arranged for supplying sample containers in the x-direction and second guide are arranged for supplying reagent containers in the y-direction to the process area, wherein the second guides extend in the y-direction at an angle $\alpha$ of 30 to 150° to the x-direction, a carrier element, which can be moved back and forth in the x-direction, comprises carrier plates which can be lifted and lowered in the z-direction, individually and together, for magnetic or magnetisable transfer elements which are arranged in a matrix shape, the reagent containers can be positioned according to the grid of the transfer elements by introduction, taking place at an angle $\alpha$, into the process area and can be rejected by ejection in the same direction into a waste collector.

Special and developing embodiments of the invention are the subject of dependent claims.

Transfer elements are preferably configured as permanent magnetic rods or as rod-shaped electromagnets.

The lowermost part of the transfer elements, which dip into the sample and reagent containers, is expediently covered with a membrane which can be lifted and lowered, can be deposited and taken off by a relative movement with respect to the transfer elements and is preferably tubular or beaker-shaped. the membrane can be omitted in the case of electromagnetically operating transfer elements.

According to the prior art, cyclic batches constantly run one-dimensionally in the x-direction. According to the invention, the cyclic batches run two-dimensionally, the sample containers in the x-direction and the reagent containers, in contrast, in the y-direction. As is conventional in the case of space coordinates, the two directions preferably have an angle $\alpha$ of 90°, and they also run at right angles with respect to the third, vertical, space coordinate z. The first guide for supplying the sample containers in the x-direction is given; it runs in the same direction as the back and forth movement of the carrier element. In special embodiments on the other hand, the y-direction for the two guides may vary in a relatively large angle range. The second guides expediently extend in parallel but they may also spread out and/or, rising, from a side. Closed reagent containers, however, at the latest directly before the process area, have a horizontal position, so they can be loaded with a reagent or a possible closure can be torn off or penetrated without risk of the reagent leaking.

The relative movement of a transfer element in the longitudinal direction thereof compared to the membrane preferably takes place by different lifting and lowering of the relevant carrier plates or guides with means which are known per se. Obviously, the relative movement could partially also take place by means of lifting and lowering the carrier block located below the reagent containers, but this seems less advantageous.

The transportation of the magnetic microparticles in the x-direction preferably takes place, as mentioned, on tubular or breaker-shaped cavities of the membrane in the lowermost region of the transfer elements when the forward movement of the carrier plates takes place in the x-direction and the pulled-up membrane can be lowered into the immediately following reagent container. These membranes are expendable materials; they are guided to the inlet side of the process area, positioned during a lowering movement, placed on the rearmost transfer elements in the x-direction and entrained. It must be possible to position the membranes in the reagent containers, about halfway up the maximum lifting height of the transfer elements, with and without an introduced transfer element. For the continuous supply of membranes to the inlet side of the process area, a third guide is provided which, with respect to the x-direction, has an angle of preferably 60 to 120°. The membranes are designed such that they can be introduced into the sample and reagent containers; in other words they are the same, in particular, with respect to number and form of the cavities. The membranes are also designed, like the sample and reagent containers, preferably as injection mouldings or deep-drawn parts made of plastics material.

The containers and the membranes are substantially strip-shaped, stackable cassettes with a plurality of beaker-shaped cavities corresponding to the grid of the transfer elements in the carrier element.

With regard to the method for automatically separating the solid and the liquid phase of a suspension and for purifying the solid phase, the object of the invention is achieved in that the forward movement of the carrier element in the x-direction takes place with the use of permanent magnetic rods as transfer elements with loaded, pulled up membranes or with the use of rod-shaped electromagnets with the current switched on, and the backward movement counter to the x-direction takes place with the use of permanent magnetic rods as transfer elements without membranes or with the use of rod-shaped electromagnets with the current switched off. Special and developing embodiments of the method are the subject of dependent claims.

Firstly, the filled sample containers are preferably guided intermittently or continuously on the longitudinal side in the x-direction and the reagent containers with different or at most partially the same fillings are guided continuously in the y-direction at the end face to the process area. With each initiation of a new operating cycle, one membrane in each case is put over the rearmost transfer elements in the x-direction, configured as permanent magnetic rods, the latter are lowered into the sample container disposed at the process area and, after attachment of the magnetic microparticles to the membrane, the transfer elements with the membrane are raised from the suspension liquids. The carrier element is displace forward in the x-direction by a grid unit, corresponding to the spacing between two reagents containers, the particle-free sample container is ejected into a waste container. The filled reagent containers are simultaneously introduced into the process area, the carrier element with the transfer elements is lowered into the reagent container, the transfer elements are pulled out of the membranes, the attached magnetic microparticles are resuspended and the suspension mixed. The transfer elements are returned by the spacing a counter to the x-direction, while the membranes remain in their position.

On each movement of the carrier plates in the x-direction, the membranes are entrained by one grid unit, the spacing a, and at the end of the process area, ejected into a waste container. The last reagent container in the x-direction, ejected from the process area, is supplied for any further use which is known per se, for example chemical analysis.

In the case of transfer elements which are configured as rod-shaped electromagnets, without a membrane, the current is switched on for loading with microparticles and switched off for suspension.

One working cycle preferably lasts 2 to 4 min. The duration of one working cycle is as low as possible for economic reasons, currently about 2 min can be achieved.

With a full working load, 6 to 10 reagent containers are simultaneously pushed into the process area. All the reagent containers preferably have different reagents, with pure water or an organic solution also being called a reagent. Obviously, however, sequences with individual ore repeating reagents my be put together. Within the same reagent container, the cavities always have the same reagent. If not all the channels (48 in FIG. 17) are occupied by reagent containers, the frontmost channels in the x-direction remain empty. The rejection of the membranes and the further use of the frontmost reagent container takes place as if it were in the frontmost channel.

The microparticles used, as the name states, have dimensions from one to a plurality of micrometres and they may also have fractions of a micrometre and should then correctly be called nanoparticles. For the sake of simplicity, however, the term microparticles will be used for all particle sizes. the cavities of the sample and reagent containers generally have a volume of 1 to 3 ml.

The advantages of the invention can be summarised as follows.

The device according to the invention can be operated fully automatically.
the method with the working cycles allows all the cavities to be in action during the entire process.
Numerous modules, generally six to ten, can operate simultaneously, which means maximum working productivity.
The matrix arrangement allows as optimally dense arrangement, resulting in a further increase in productivity.
The method allows continuous processing of samples.

The invention will be described in more detail with aid of embodiments shown in the drawings, which are also subject of dependent claims. In the drawings, schematically:

FIG. 1 shows a perspective view of the device,

FIG. 2 shows a vertical section in the x-direction through the process area, FIG. 3 shows a layout of the device at the beginning of the process, FIG. 4 shows a vertical section in the x-direction through the process area with the positioned sample container, FIG. 5 shows a subsequent process step according to FIG. 4, with the permanent magnetic rods dipped in the sample container, with membranes, FIG. 6 shows a next process step according to FIG. 5 with a carrier element displace in the x-direction, FIG. 7 shows a layout of the device after filling of the first reagent container, FIG. 8 shows a further process step according to FIG. 6 with the permanent, magnetic rods pulled up and the membrane in the first reagent container, FIG. 9 shows a further variant with a carrier element returned in the counter direction to the x-direction, FIG. 10 shows a further method step according to FIG. 9 with the second membrane in place, FIG. 11 shows a further method step according to FIG. 10 with lowered permanent magnetic rods, FIG. 12 shows a further layout with an ejected first reagent container, FIG. 13 shows a further layout of the device with the carrier element moved forward in the x-direction, FIG. 14 shows a further method step according to FIG. 13 with the carrier element displaced in the x-direction, FIG. 15 shows a further layout after a plurality of method steps with the first reagent container in the end position, FIG. 16 shows a last layout with an ejected reagent container and membrane, FIG. 17 shows a partially cut away perspective view of a carrier block, FIG. 18 shows a horizontal section through a magnetic mixer, FIG. 19 shows the magnetic mixer according to FIG. 18 in the other position, and FIG. 20 shows the lowermost region of cavity of a sample or reagent container.

A perspective view of a device 10 according to the invention with the preferably right-angled space coordinates x, y and z substantially comprises a central process area 12, where the separation and purifying processes take place, first guides 14, indicated only by dashed lines, for sample containers P and second guides 18 for reagent containers R. The first guides 14 in the x-direction and the second guides 18 in the y-direction have an angle α of 90°, in other words extend at right angles. Both the samples P and the reagent containers R are substantially strip-shaped and have tubular or breaker-shaped cavities 22, which are produced by injection moulding from plastics material, the sample containers P and reagent containers R being identical. A peripheral flange 16 does not only stabilise the cavities 22, it is also used for guidance and holding.

The process area 12 is limited in the horizontal extent, largely by a carrier element 24, which consists of three carrier plates 24a, 24b and 24c. The entire carrier element 24 is lifted and lowered in the z-direction with the lowermost carrier plate 24a, and the drive and the control for this are implemented with means which are known per se, like the drive for supplying the sample containers P and the reagent containers R. The carrier plates 24b and 24c can be lifted and lowered together, but also individually, resulting in a relative displacement. In this case, the transfer elements 28, which are configured as permanent magnetic rods, are pushed into the membranes M or pulled out therefrom.

The carrier element 24 has a predetermined grid of holes 30, which are penetrated by permanent magnetic rods 28. These have peripheral collars, which rest on the carrier plate 24c. The membranes M are basically configured like the sample containers P and reagent containers R, but the cavities 32 are generally cylindrical. A prepared membrane M is supplied from the front left with a third guide, which is not shown for the sake of clarity. The membranes M are received at the entry to the process area 12 and conveyed during each working cycle by the grid distance a in the x-direction. This takes place by means of displacement on a horizontal pair of rails 36.

During each working cycle one filled sample container P, on the longitudinal side, reaches the process area 12. Magnetic microparticles (76 in FIG. 20) attach to the membranes M or its cavities 32 at the frontmost sample container P in the x-direction, when the permanent magnetic rods 28 are introduced. These microparticles are conveyed stepwise from reagent container R to reagent container R by way of the membranes M, with it being possible to resuspend the attached microparticles in each working cycle. The sample containers P are ejected in the y-direction and collected in a waste container, not shown.

The reagent containers R which are supplied in the y-direction have also been filled in-line. If preassembled, filled reagent containers R are used, these are torn open or penetrated in the lid region directly before the process area 12, so a membrane M or the permanent magnetic rods 78 can be supplied. The mechanisms for filling or opening are arranged in or on a housing 38 which can also be lifted or lowered in the z-direction. In the working cycle, in the present case, six reagent containers R are introduced into the process area 12 and the used containers are ejected in the y-direction into a waste collector. Neither sample containers P nor reagent containers R are guided in the x-direction through the process area 12.

In each working cycle of about three minutes in duration, 48 samples are simultaneously separated or purified or washed. Per working cycle, eight samples leave the process 12, in other words about 160 samples in an hour.

In FIG. 2, the process area 12 is shown at the beginning of a working cycle. The carrier plates 24a and 24b are lifted to such an extent that the membranes M are located above the level of the suspension 40 in the reagent containers R. The uppermost carrier plate 24c is lifted to such an extent that the permanent magnetic rods 28 are practically pulled out of the membranes M. The frontmost sample container P in the x-direction, the advance direction, is still outside the process area 12.

A holder 34 with a membrane M is moved to the process area 12, and the membrane M can be put over the permanent magnetic rods 28 in the z-direction. This is the first process step of a working cycle. The path of the membranes M through the entire process 12 in the x-direction is indicated by arrows 44.

Channels 48 for the reagent containers R which are inserted from the rear, positioned in the working position according to the grid of the permanent magnetic rods 28, and ejected to the front, which channels are open on either side, extend perpendicularly to the x-direction in the carrier block 46. Configured in an alternating manner with respect to channels 48, which are open laterally and upwardly are recesses 50, in which beams 52 which can be pushed back and forth, i.e. perpendicularly to the drawing plane, in the y-direction, are arranged, with permanent magnets, shown later in detail, for mixing the suspension 40.

A layout according to FIG. 3 shows—viewed from the top—the process area 12, in which neither sample containers P, nor reagent containers R, nor membranes M are introduced. A sample container P1 placed according to the grid in x-direction at a spacing a is covered by a membrane M1, which is put over the permanent magnetic rods 28 from below. A further section 53 contains the sample containers P2 to P7, which are fed in by filling station 54.

In the y-direction, six reagent containers R1.1 to R6.1 have been pushed at the end face to the process area 12. In this position, the reagent containers R are opened or filled with reagents. The reagent containers R of a buffer section 58 are designated by R2.1 to R6.2.

FIG. 4 shows the situation according to FIG. 3 in vertical section in the x-direction. The rearmost permanent magnetic rods 28 in the x-direction have the membrane M1 put over from below. In the x-direction, the frontmost sample container P1 is lined up at the process area 12. The latter is located precisely below the membrane M1. The holder 34 of the membrane M1 is ejected and disposed of after the membrane M1 has been lifted, and this is indicated by an arrow.

In FIG. 5 the par of rails 36 and the carrier element 24 are completely lowered in the direction z and the membranes M1 are dipped with the inserted permanent magnetic rod 28 into the suspension of the sample container P1 placed on the longitudinal side at the process area 12. Under the action of the permanent magnetic rods 28, the magnetic microparticles of the suspension settle on the membrane M1 and remain suspended on the membrane 26 when the pair of rails 36 and the carrier element 24 are raised.

FIG. 6 shows the pair of rails 36 and carrier element 24 which have been raised to the same degree. In this position, the carrier element 24 has been displaced in the x-direction by the grid spacing a. The rearmost permanent magnetic rods 28 in the x-direction with the membrane M1 placed over are now precisely above the reagent container R.1.1 which has been introduced in the meantime. The membrane M1 has been pushed into this position according to FIG. 6 in the pair of rails 36. The reagent container 1.2, according to FIG. 7, has slipped from the buffer section 58 into the buffer section 52 where it is filled with reagents or the seal is pushed in. The reagent container R1.3 has been moved up onto the buffer section 58.

Compared to the layout according to FIG. 3, the sample container P1 has been pushed away in the y-direction and falls into a waste collector, not shown. This is indicated by an arrow 60.

It is shown in FIG. 8 that the carrier element 24 with the carrier plates 24a, 24b and 24c are lowered to such an extent that the first membrane M1 has been dipped into the reagent container R1.1. Under the magnetic effect, the microparticles collect on the surface of the membrane M1. After a reaction time of about 1 minute, the carrier plate 24c with the permanent magnetic rods 28 is pulled out of the membrane M1. A magnetic mixing mechanism 62 is now started up. The magnetic microparticles are released by the mixing mechanism 62 from the membrane M1 and are resuspended.

In the next working step according to FIG. 9, the complete carrier element 24 is raised until the permanent magnetic rods 28 are completely removed from the membrane M1 which was also raised with the pair of rails 36. A second membrane M2 is then provided. The carrier element 24 can now be returned counter to the x-direction by one grid unit a and the rearmost permanent magnetic rods 28 in the x-direction are now precisely above the provided second membrane M2.

In the subsequent method step according to FIG. 10 the carrier element 24, consisting of three carrier plates 24a, 24b and 24c, are moved down in the z-direction, until the second to rearmost permanent magnetic rods 28 in the z-direction have been dipped into the first membranes M1 in the working position. At the same time, the second membranes M2 are put over the permanent magnetic rods 28.

In FIG. 11, three process steps are combined. Finally, the holder 34 for the second membrane M2 is removed, which is characterised by an arrow. then, the second to frontmost sample container P2 in the x-direction is guided to the process area 12, and finally the carrier 24 is lowered to such an extent that the first membrane M1 is dipped into the first sample container P1.1 and the second membrane M2 is dipped into the second to frontmost sample container P2 and the corresponding permanent magnetic rods 28 have been lowered into the membrane M2. The microparticles are now attached to the two first membranes M1, M2. When the permanent magnetic rods 28 are pulled up, they can be removed from the liquid phase of the suspension. The microparticle-free reagent container R1.1 can now be pushed out of the process area 12 in the y-direction and this is shown in the layout of FIG. 12. Only the first membrane M1 remains in the process area 12.

According to the following layout shown in FIG. 13, the second sample container P2 is also ejected in the y-direction and fed to the waste collector. The process containers R1.2 and R2.1 are pushed up into the process area 12 and positioned below the membranes M1 and M2.

According to FIG. 14, the carrier element 24 with the permanent magnetic rods 28 and the membranes M1 is pushed forward by a grid unit a in the x-direction and then lowered as a whole in the z-direction until the membranes M1 and M2 are positioned in the two first reagent containers R1.2 and R2.1. The magnetic microparticles are now collected on the outer wall of the membranes M1 and M2 and are attached. In the new working cycle started with FIG. 9, the procedure is now as in the previous working cycle: lifting the permanent magnetic rods 28, mixing the releasing magnetic microparticles etc. Each new working cycle is started with placing of a membrane M and the removal of the samples from the frontmost sample container P lined up in the x-direction, on the longitudinal side at the process area 12.

In the layout according to FIG. 15, the membrane M1 has reached the last working position in the x-direction in the process area 12. The treatment of the samples has been competed; all the provided operations have then been carried out. Only in this configuration is the device fully operable.

In the layout according to FIG. 16, it is shown that the first membrane M1, which has run through all the working cycles, is fed to the waste collector after ejection from the process area 12. The reagent container 6.1 with the result of the six working cycles, on the other hand, is supplied for use, which is indicated by the arrow 64.

FIG. 17 shows a carrier block 46, which has been broken open for the sake of clarity, of the process area 12. There are six continuous channels 48 which are open at the top, for the message of the reagent containers R. When passing through, the reagent containers R slide with their peripheral flange 16 in opposing grooves 66 in the side walls 47 of the channels 48.

Provided between the channels 48 of the carrier block 46 are further recesses 68, which alternate with the channels 48 and are closed on the end face 70 of the carrier block 46. The recesses 68 are used for receiving beams 72, which can be pushed back and forth in the y-direction, with integrated permanent magnets 74. The permanent magnets 74 are arranged in the region of the cavities 22 of the reagent containers R and are used for mixing the resuspended magnetic microparticles 76.

As can be seen from FIGS. 18 and 19, the beans 72a, 72b which can be moved back and forth are arranged on either side of cavities 22 of a reagent container R. The permanent magnets 74 are arranged in the double spacing of the cavities 22. When switched on, there is a relative movement between the permanent magnets 74 and the cavities 22. The microparticles 76 which are attached on the side, change side, so an effective mixing effect is produced. The effect can be improved in that the cavities are configured so as to be elliptical, oval or rectangular with round short sides.

FIG. 20 shows a greatly enlarged view of the lower region of a cavity 22 with a suspension 78. The lowermost region of a permanent magnetic rod 28 is covered with a beaker-shaped membrane M. The permanent magnets 28 have the effect that the microparticles 76 collect on the membrane M or the cavities 32. If the membrane M is removed together with the permanent magnetic rods 28, the microparticles 76 are lifted from the practically particle-free suspension 78. If, on the other hand, the permanent magnetic rod 28 is removed and the membrane M left, the microparticles 76 are released again from the membrane M. By mixing, for example as shown in FIGS. 18 and 19, the release process can be accelerated and the mixing effect improved.

The invention claimed is:
1. Device (10) for the automatic separation of the solid and liquid phase of a suspension (78) and for purifying magnetic microparticles (76) loaded with organic, substances, which device (10) comprises a process area (12), and a first guide (14) which is arranged for supplying sample containers (P)

with magnetic microparticles in the x-direction to the process area (12) and second guide (18) which is arranged for supplying reagent containers (R) in the y-direction to the process area (12) and ejection of the reagent containers in the same direction into a waste collector, wherein the second guide (18) extends in the y-direction at an angle (α) of 30 to 150° to the x-direction, and additionally, the device comprises a carrier element (24), which can be moved back and forth in a cyclic manner in the x-direction, which carrier element comprises several carrier plates (24a, 24b, 24c) that can be lifted and lowered individually in the z-direction, running essentially perpendicular to the x- and y-direction, and wherein at least one of the carrier plates carries a plurality of magnetic or magnetisable transfer elements (28) arranged in a grid-like manner, whereby, by lowering the at least one carrier plate, the transfer elements can be lowered in z-direction into sample containers or reagent containers for magnetically attaching magnetic microparticles located in said containers and after lifting the transfer elements in z-direction, transporting the magnetic microparticles attached to the transfer elements in x-direction by movement of the carrier element, and after lowering the transfer elements in z-direction into further reagent containers releasing the magnetic microparticles attached to the transfer elements into the further reagent containers, whereby the reagent containers are positioned according to the grid of the transfer elements (28).

2. Device (10) according to claim 1, wherein the transfer elements (28) are configured as rod-shaped permanent magnets or electromagnets.

3. Device according to claim 1 or 2, wherein a lowermost part of the transfer elements (28) entering into the sample containers (P) or reagent containers (R) when lowering the transfer elements in z-direction is covered by a tubular or beaker-shaped membrane (M) which can be attached to the transfer elements and taken off from the transfer elements by means of a relative movement in the z-direction with respect to the transfer elements (28).

4. Device according to claim 3, wherein the relative movement of a transfer element (28) to the corresponding membrane (M), in the z-direction thereof, takes place by means of different lifting or lowering of the carrier plates (24b, 24c).

5. Device (10) according to claim 1, wherein the angle (α) between x- and y-direction is 90°.

6. Device (10) according to claim 1, wherein a third guide is arranged for continuously supplying the membranes (M) at an angle (β) of 60 to 120° with respect to the x-direction.

7. Device (10) according to claim 1, wherein a carrier block (46) with channels (48) for guiding the reagent containers (R) is arranged in the process area (12), which channels extend perpendicularly to the x-direction, and each of the channels has two horizontal grooves (66) in the side walls (47) which are opposing at the same level and open on the end face.

8. Device (10) according to claim 7, wherein beams (72) which can be displaced horizontally back and forth, comprising permanent magnets (74) arranged in the region of the lowerable transfer elements (28), are arranged in recesses (50) extending parallel to the channels (48), to resuspend and mix the microparticles (76).

9. Device (10) according to claim 1 further comprising sample and reagent containers (P, R) and membranes (M) which are configured as substantially strip-shaped, stackable cassettes with a plurality of beaker-shaped cavities (22, 36) corresponding to the grid of the transfer elements (28) in the carrier element (24).

10. Device (10) according to claim 9 wherein the sample and reagent containers feature six to ten cavities (22) with flat or oval cross-sections, and wherein cross-sectional internal diameters of the sample and reagent containers are larger than corresponding dimensions of the transfer elements (28) with pulled-on membranes (M).

11. Method for automatically separating the solid and liquid phase of a suspension and purifying the solid phase with a device (10), sample containers (P) and reagent containers (R) according to claim 1 wherein a forward movement of the carrier element (24) in the x-direction takes the place with the use of permanent magnetic rods as transfer elements (28) with loaded, pulled-up membranes (M) or with the use of rod-shaped electromagnets with an electric current switched on, and a backward movement counter to the x-direction takes place with the use of permanent magnetic rods as transfer elements (28) without membranes (M) or with the use of rod-shaped electromagnets with the electric current switched off.

12. Method according to claim 11, wherein the filled sample containers (P) are firstly guided intermittently or continuously on the longitudinal side in the x-direction and the reagent containers (R) with different or at most partially the same fillings are guided continuously in the y-direction ant the end face to the process area (12), on each initiation of a new operating cycle, one membrane (M) in each case is put over the rearmost transfer elements (28) in the x-direction, the latter are lowered into the sample container (P) disposed at the process area (12) and, after attachment of the magnetic microparticles (76) to the membrane (M), the transfer elements (28) with the membrane (M) are raised from the suspension liquids, the carrier element (24) is displace forward in the x-direction by a grid unit, corresponding to the spacing (a) between two reagent containers (R), the particle-free sample container (P) is ejected into a waste container, the filled reagent containers (R) are simultaneously introduced into the process area (12), the carrier element (24) with the transfer elements (28) are pulled up of the membranes (M), the attached magnetic microparticles (76) are resuspended, the suspension (78) mixed, the transfer element returned by the spacing (a) counter to the x-direction, while the membranes (M) remain in their position.

13. Method according to claim 11 or 12, wherein upon each movement of the carrier element (24) in the x-direction, the membranes (M) are entrained by one grid unit and are ejected at the end of the process area (12) into a waste collector.

14. Method according to claim 11, wherein the last reagent container (R) in the x-direction, which is ejected from the process area (12), is supplied for a further use.

15. Method according to claim 11, wherein a working cycle lasts 2 to 4 min.

16. Method according to claim 11, wherein the reagent containers (R) are used with different reagents, but with the same reagent in all the cavities (22) of the same reagent container (R).

* * * * *